United States Patent
Bailey, III

(10) Patent No.: US 7,403,001 B1
(45) Date of Patent: Jul. 22, 2008

(54) METHODS AND APPARATUS FOR MEASURING MORPHOLOGY OF A CONDUCTIVE FILM ON A SUBSTRATE

(75) Inventor: Andrew D. Bailey, III, Pleasanton, CA (US)

(73) Assignee: Lam Research Corporation, Fremont, CA (US)

( * ) Notice: Subject to any disclaimer, the term of this patent is extended or adjusted under 35 U.S.C. 154(b) by 660 days.

(21) Appl. No.: 11/093,400

(22) Filed: Mar. 29, 2005

(51) Int. Cl.
*G01N 27/72* (2006.01)
*G01R 33/12* (2006.01)
*G01R 33/14* (2006.01)
*G01B 7/06* (2006.01)

(52) U.S. Cl. .................. 324/239; 324/229; 324/222
(58) Field of Classification Search ............. 324/222, 324/228–243
See application file for complete search history.

(56) References Cited

U.S. PATENT DOCUMENTS

| | | | | |
|---|---|---|---|---|
| 3,922,599 A | * | 11/1975 | Steingroever et al. | 324/230 |
| 4,763,071 A | * | 8/1988 | McGee et al. | 324/233 |
| 5,343,146 A | * | 8/1994 | Koch et al. | 324/230 |
| 6,072,313 A | * | 6/2000 | Li et al. | 324/230 |
| 6,933,178 B1 | * | 8/2005 | Su | 438/126 |
| 7,151,366 B2 | * | 12/2006 | Renken et al. | 324/158.1 |
| 7,288,941 B2 | * | 10/2007 | Redko et al. | 324/450 |
| 2003/0141572 A1 | | 7/2003 | Wilby | |
| 2004/0155667 A1 | * | 8/2004 | Kesil et al. | 324/663 |

* cited by examiner

*Primary Examiner*—Reena Aurora
*Assistant Examiner*—Kenneth J Whittington
(74) *Attorney, Agent, or Firm*—IP Strategy Group, P.C.

(57) ABSTRACT

A method of determining a mass variation of a conductive film on a substrate with an area, an edge zone, and a center zone, is disclosed. The method includes providing a measured conductive film mass of a conductive film on a substrate. The method also includes positioning a sensor near a set of positions on the substrate; measuring using the sensor a set of electrical responses; and correlating the set of electrical responses to a set of conductive film thicknesses. The method further includes estimating a volume of the conductive film based at least in part on the set of conductive film thicknesses and the area; and estimating a derived conductive film mass based in part on the volume and a conductive film density, wherein the mass variation is a difference between the measured conductive film mass and the derived conductive film mass.

25 Claims, 5 Drawing Sheets

METHODS AND APPARATUS FOR MEASURING MORPHOLOGY OF A CONDUCTIVE FILM ON A SUBSTRATE

BACKGROUND OF THE INVENTION

The present invention relates in general to substrate manufacturing technologies and in particular to methods and apparatus for measuring morphology of a conductive film on a substrate.

In the processing of a substrate, e.g., a semiconductor wafer, MEMS device, or a glass panel such as one used in flat panel display manufacturing, plasma is often employed. As part of the processing of a substrate (chemical vapor deposition, plasma enhanced chemical vapor deposition, physical vapor deposition, etc.) for example, the substrate is divided into a plurality of dies, or rectangular areas, each of which will become an integrated circuit. The substrate is then processed in a series of steps in which materials are selectively removed (etching) and deposited (deposition) in order to form electrical components thereon.

Metals are particularly important materials in substrate manufacturing. For example, in a manufacturing method, known as dual damascene, dielectric layers are electrically connected by a conductive plug filling a via hole. Generally, an opening is formed in a dielectric layer, usually lined with a TaN or TiN barrier, and then subsequently filled with other conductive material (e.g., aluminum (Al), copper (Cu), tungsten (W), etc.) that allows electrical contact between two sets of conductive patterns. This establishes electrical contact between two active regions on the substrate, such as a source/drain region. Excess conductive material on the surface of the dielectric layer is typically removed by chemical mechanical polishing (CMP). A blanket layer of silicon nitride or silicon carbide may then be deposited to cap the copper.

Subsequently, it's generally important to insure that the process is within acceptable parameters. For example, if a process involves multiple steps, each with its own gas mixture, gas pressure, RF voltage and power settings, and duration, it is difficult to ascertain exactly, by examining a post-process substrate, which parameter in which step did not conform to specifications and is thus likely to be the source of the defects. In metrology, one can refer back to the log file to obtain more information but the process is not integrated and requires one or more substrate runs (and possibly ruining one or more substrates) before the problem is spotted.

Furthermore, the whole cycle of processing a substrate, examining the processed substrate, and troubleshooting the plasma processing system based on the data obtained from the processed substrates may take a substantial amount of time. If multiple cycles are required to remedy a manufacturing, installation, or qualification problem, the multiple cycle times increase the total time and effort required to bring a plasma processing system on line for production, thereby contributing to a higher cost of ownership even before a single production IC is created.

Once a plasma processing system is placed into production, the processed substrates outputted by the plasma processing system are periodically examined to obtain information about system performance. While equipment manufacturers try to create a maintenance schedule that cleans and/or replaces parts before problems arise, equipment failure would still occur sometimes. Since raw substrates, processed gases, and plasma processing systems are all expensive, IC manufacturers are motivated to detect failures as quickly as possible to minimize further damage to substrates and/or other subsystems of the plasma processing system and to remedy the failure found to bring the plasma processing system back on line quickly.

In the typical case, once it is ascertained that the processed substrate contains an unacceptably high number of defects, a specialist may be called upon to troubleshoot the plasma processing system. An experienced specialist may be able to guess fairly accurately, based on his/her experience and the data obtained from the defective substrates, the possible sources of the defect and to perform the appropriate maintenance steps to address those possible sources of defect. Once the maintenance steps are performed, one or more substrates may be processed, and the output substrates may be examined again to determine whether the defects have been remedied. If they persist, other maintenance steps may be performed and other substrates may be processed to again ascertain whether the defects have been remedied. The cycles of performing one or more maintenance steps and examining the output substrates for defects may continue until the defects are remedied.

Occasionally, the IC manufacturer and/or the system vendor may wish to upgrade the hardware and/or software of a plasma processing system to address a problem or to improve the system's capabilities. Once new hardware and/or software is installed, it is not unusual to run one or more batches of substrates through the newly upgraded plasma processing system and to examine the processed substrates to ensure that the upgraded plasma processing system performs as designed.

Again, while the processed substrates can furnish certain data useful in monitoring the production of ICs in installed and/or upgraded plasma processing systems, there are disadvantages associated with relying primarily on substrates data to guide the operation and/or maintenance of the plasma processing system. As discussed in the earlier example, if a process involves multiple steps, each with its own gas mixture, gas pressures, RF voltages and power settings, and duration, it is difficult to ascertain exactly, by examining a post-process substrate, which parameter in which step did not conform to specifications and is thus likely to be the source of the defects. Furthermore, the whole cycle of processing a substrate, examining the processed substrate, and troubleshooting the plasma processing system based on the data obtained from the processed substrates may take a substantial amount of time. If multiple cycles are required, the multiple cycle times increase the total time and effort required to remedy the failure and to bring the plasma processing system back on line for production use, thereby contributing to a higher average cost per substrate successfully processed.

One common method of determining that a process is within acceptable parameters is to measure the electrical film properties (e.g., thickness, sheet resistance, etc.) of a conductive layer at a particular point on the substrate, particularly by using eddy current sensors. Generally, eddy currents are currents that are induced in a conductive media by an alternating magnetic field. Generally, a larger physically continuous conductive mass produces a larger eddy current response, while a smaller physically non-continuous mass produces a smaller eddy current response. Likewise, a lower temperature generally increases conductivity, and hence the resulting the eddy current response, while a higher temperature generally reduces conductivity, and hence the resulting eddy current response as well.

In general, if a first alternating current is applied to a wire wrapped in a generally solenoidal shape (e.g., the wire in an eddy current sensor), a first alternating electromagnetic field forms in and around the solenoid extending beyond the ends of the solenoid a distance on the order of the diameter of the solenoid. If this first field is brought into proximity with a second conductor (e.g., a conductive layer on the substrate) a second alternating electrical current will also flow in the second conductor, causing a second field that interacts with (e.g., adds vectorally to) the first field and results in a perturbation to the field around the probe. These perturbations in the probe's initial field may cause detectable changes in the probe's electrical characteristics including the probe's impedance and frequency response. Using an impedance-voltage converter, the impedance change can be converted into a voltage change for further signal processing and analysis.

Many techniques are available for producing a signal from these detected differences in eddy current probe characteristics. For example, in a first technique, the width of the frequency dependent power absorption of the probe/eddy current sensor system (sensor system) can be reported. Likewise, in a second technique, the change in the magnitudes of the real and/or imaginary parts of the probe impedance can be reported between the probe and the second conductor. These measurements are generally made using passive or active circuitry to produce a range of voltages that can be bounded by the signal with no second conductor present and the signal with a second conductor causing maximal change in the signal. The exact shape, thickness and conductivity of the second conductor that causes the maximal change in the probe signal generally depends on the probe geometry, excitation frequency and the method adopted for measurement, but generally it is a thick (on the order of many times the diameter of the probe) conductive film placed as near to the probe as possible.

Depending on the application, conductive or magnetic elements can also be incorporated into the design of the probe in order to modify the spatial extent and magnitude of the probe field and hence the spatial and electrical sensitivity to the second conductive layer. For optimum performance, the sensor system should maximize sensor system sensitivity to the desired electrical property of the conductive film (e.g., thickness, sheet resistance, etc.) while minimizing the sensor system's sensitivity to all other effects and variables.

However, the electrical response of sensor to the magnetic field (eddy current perturbations), and hence its accuracy, may also be affected by the proximity (substrate proximity response) of the sensor to the substrate. That is, as the exciting probe field is of limited spatial extent and its magnitude decreases as the position increases from the probe, the overall eddy current perturbations caused by a second conductor being measured also decrease as the second conductor is moved further from the probe. Thus, an eddy current sensor may be sensitive to both proximity and electrical film properties. In general, it is difficult to isolate the portion of the electrical response caused by electrical film properties (electrical film property response) from the portion of the electrical response caused by proximity (substrate proximity response), which may subsequently introduce an error in the reported value.

Referring now to FIG. 1A, a simplified diagram of an eddy current sensor is shown. Generally, changes in the sensor's coil impedance 102 are caused by varying the distance 104 between the sensor (coil) and substrate 106. Since the electrical parameters of target material resistivity and permeability may determine the magnitude of the measured sensor perturbation, the sensor system is generally calibrated for the target material.

Referring now to FIG. 1B, a more detailed diagram of a sensor head of the eddy current sensor of FIG. 1A is shown. As previously described, sensor coil 102 generates a first alternating electromagnetic field 204 that when brought into proximity by a distance 104 with a second conductor on the substrate 106, a second alternating electromagnetic field 206 will also flow in the substrate that can be correlated to the thickness of a metal film. In addition, the direction 104 refers to the effective measuring proximity of sensor coil 102 and is usually on the order of a few radii of the coil 102. In general, the larger the first alternating electromagnetic field 208, the greater the area that can be measured.

Referring now to FIG. 2, a simplified diagram of a substrate on a turntable with an eddy current sensor arm is shown. Although in this example, substrate 202 rotates in direction 208, as sensor swing arm 204 moves sensors 206 across the surface of substrate 202, other configurations which move the sensors relative to the substrate exist.

Eddy current measurements generally assume an infinite plane of conductive film. For example, one method of eddy current measurements is to consider an infinite plane of conductive film placed a certain proximity to a set of parallel eddy current sensors. Usually the desired sensor system reported output is the film thickness, where factors such as conductivity, connectivity, grain structure, etc. are assumed to be constant, or alternatively, to have a negligible effect on the raw measured eddy current signal.

However, common methods of eddy current measurement presume the lack of edge effects to create eddy current discontinuities. In practice, this assumption tends only to exist in the center area of the substrate (center zone), since in the area near the substrate edge (edge zone) there may exist a discontinuity in the film caused by the absence of the substrate which does not follow the assumption of an infinite plan.

As previously described, eddy current sensors generally depend on creating an oscillating magnetic field and detecting the changes caused by the presence or absence of conductive material within the region of oscillating (vacuum) fields. Since a common way to make a magnetic field is with a coil of current carrying wire, the size of the eddy current sensors' sensing region (transverse size) is generally on the order of the size of the coil or magnetic material sheathing which can modify the flux shape at the sensor tip. That is, the smaller the coil or magnetic sheathing at the tip, the more spatially restricted and hence the more spatially sensitive (and expensive) the eddy current sensor.

Subsequently, reducing the size of the coil would only reduce the discontinuity effect of the substrate edge, and not eliminate it. Additional problems with sensor system repeatability and complexity may plague a solution attempting to reduce the edge effect by reducing the spatial size of the eddy current inducing field region. This can be understood because essentially the same magnitude of field is required to induce detectible perturbations in the coil due to film properties as in a large sensor, the gradient of the eddy current inducing field strength is much larger near a small coil than near a comparably film sensitive larger sensor.

One solution may be matrix deconvolution in which the measured spatial sensitivity of the sensor is expressed as a matrix. That is, the total sensor signal is generally expressed as a summation of the sensor's sub-local spatial sensitivities times and the as yet unknown film at the sub-local location. Given that the sensor sensitivities can be measured, by measuring at many points a matrix problem for the unknown film thicknesses can be determined. However, this method tends to be sensitive to the data input. Subsequently, many more measurements may be required to achieve a sufficient level of accuracy, substantially slowing down the measuring process.

Another solution may be the use thin conductive film measurement tools with reasonably small spatial resolution with either less smaller edge effects or of sufficient spatial restriction that the effects are not of interest for the measurement application. For example, the use of four point probes with about a 3 mm resolution and reasonably well understood edge compensation models, or the use of laser based surface acoustic wave detection less than 1 mm, etc. However, although thin conductive film measurement tools may measure various convolutions of quantities (i.e., metal film conductivity, metal film thickness, crystalline structure, film stack, sensor geometry, contact resistance, etc.), the raw data from the measurements must generally be processed at a later time in order to determine conductive film thickness.

In view of the foregoing, there are desired methods and apparatus for measuring morphology of a conductive film on a substrate.

SUMMARY OF THE INVENTION

The invention relates, in one embodiment, to a method of determining a mass variation of a conductive film on a substrate with an area, an edge zone, and a center zone. The method includes providing a measured conductive film mass of a conductive film on a substrate. The method also includes positioning a sensor near a set of positions on the substrate; measuring using the sensor a set of electrical responses; and correlating the set of electrical responses to a set of conductive film thicknesses. The method further includes estimating a volume of the conductive film based at least in part on the set of conductive film thicknesses and the area; and estimating a derived conductive film mass based in part on the volume and a conductive film density, wherein the mass variation is a difference between the measured conductive film mass and the derived conductive film mass.

The invention relates, in another embodiment, to a method of determining a mass variation of a conductive film on a substrate with an area and a measured conductive film mass. The method includes measuring a set of electrical responses to the conductive film. The method also includes correlating the set of electrical responses to a set of conductive film thicknesses; and estimating a volume of the conductive film based at least in part on the set of conductive film thicknesses and the area. The method further includes estimating a derived conductive film mass based in part on the volume and a conductive film density, wherein the mass variation is a difference between the measured conductive film mass and the derived conductive film mass.

The invention relates, in another embodiment, to an apparatus for determining a mass variation of a conductive film on a substrate with an area and a measured conductive film mass. The apparatus includes means for measuring a set of electrical responses of the conductive film. The apparatus also includes means for correlating the set of electrical responses to a set of conductive film thicknesses; and means for estimating a volume of the conductive film based at least in part on the set of conductive film thicknesses and the area. The apparatus further includes means for estimating a derived conductive film mass based in part on the volume and a conductive film density, wherein the mass variation is a difference between the measured conductive film mass and the derived conductive film mass.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

While not wishing to be bound by theory, it is believed by the inventor herein that the morphology (i.e., texture, topography, etc.) of a conductive film on a substrate may be measured through the use of eddy currents. That is, eddy current conductivity correlation may be confounded with film thickness variation at particular thickness positions on the substrate, in order to determine conductive film morphology. In addition eddy current variations can be further normalized with a measured mass of the substrate. Subsequently, deviations in film properties due to changes in the metal conductivity can thus be detected (e.g., different grain sizes after annealing, different additive, concentrations in a plater, a set of changes in plating recipes, a rough substrate surface, substrate voids, overburden, etc.).

Figure 1A:
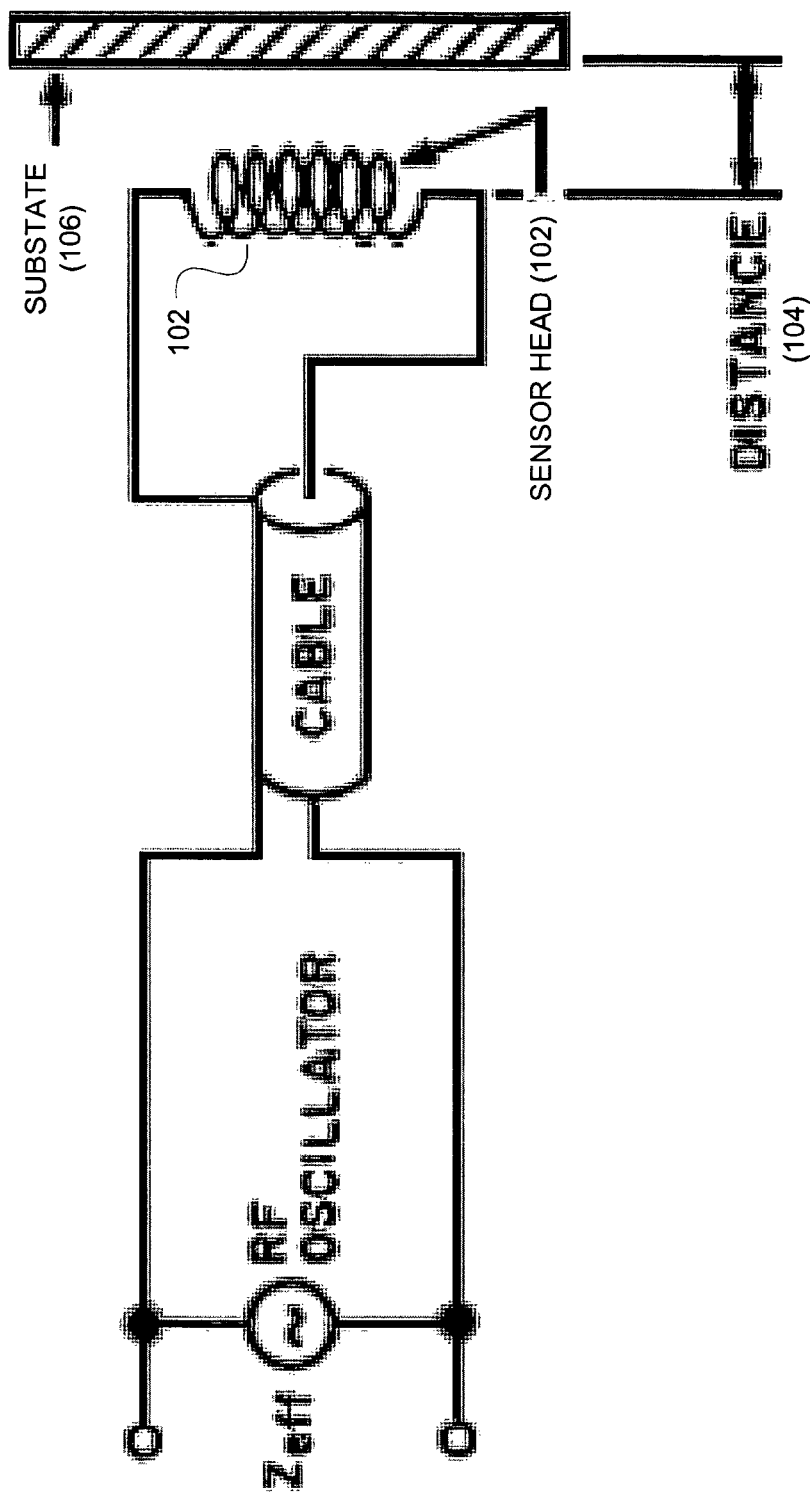
FIG. 1A illustrates a simplified diagram of an eddy current sensor.
Figure 1B:
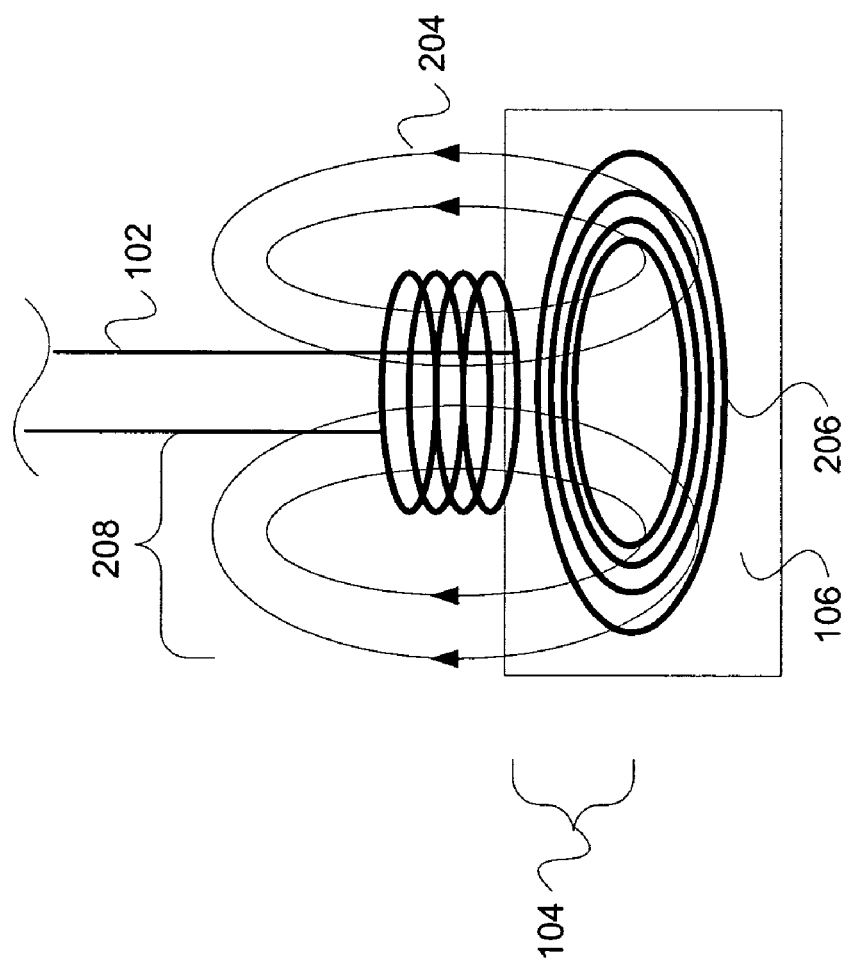
FIG. 1B illustrates a simplified diagram of the sensor hear of the eddy current sensor of FIG. 1A.
Figure 2:
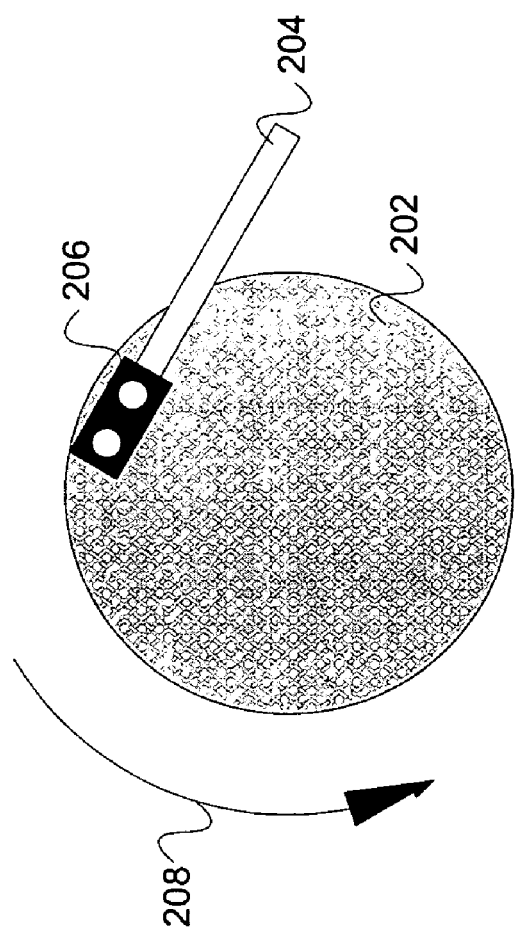
FIG. 2 illustrates a simplified diagram of a substrate on a turntable with a sensor arm.
Figure 3:
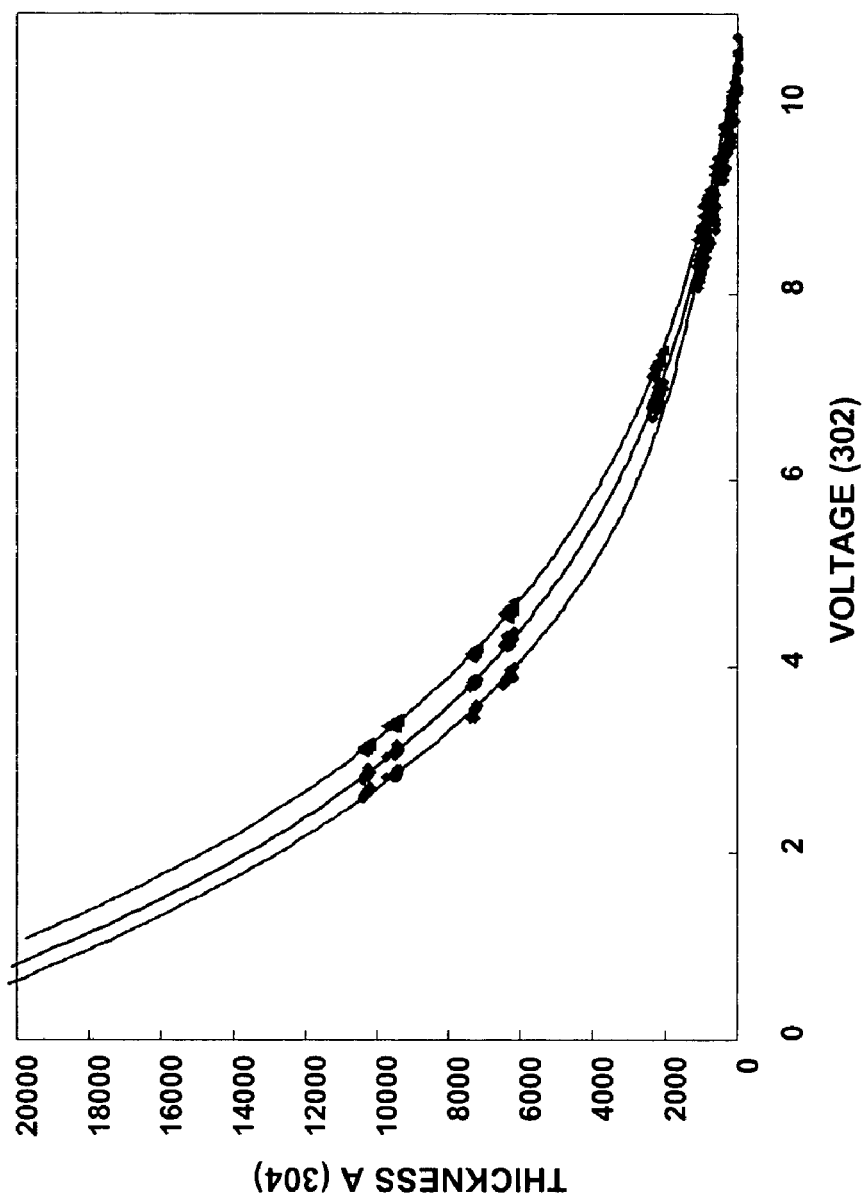
FIG. 3 illustrates a set of three calibration curves for correlating an eddy current response to a conductive layer (i.e., Cu, etc.) thickness on a substrate, according to one embodiment of the invention.

Referring now to FIG. 3, a set of three calibration curves for correlating an eddy current response to a conductive layer (i.e., Cu, etc.) thickness on a substrate is shown, according to one embodiment of the invention. The vertical axis shows thickness 304 measured in Angstroms (A), while the horizontal axis shows the voltage response (V) 302 as measured by the eddy current sensor. In this example, a higher response voltage correlates to a smaller thickness. Calibration curves may also be created for the same purpose with the response voltage decreasing, e.g., by offsetting each probe response voltage by its maximum voltage obtained in the system with no film to be measured.

In an embodiment, a set of calibration curves may be created with a mathematical optimization function. In an embodiment, the mathematical optimization function is an arc tangent function. In general, it may be reasonable to assume that the eddy current transition off the substrate, where there is no conductive film, to on the substrate, where there is a normal amount of conductive film, will have a general plot shape, such as a suitably scaled arc tangent of the distance from the edge. Actual eddy current measurement data may then be normalized with respect to measured difference of the 'on substrate' thickness of the conductive film and the 'off substrate measurement', and subsequently compared to the general plot. If a measurement is higher than the calculated transition plot, more conductive film may be present than normal, if lower, less may be present. Calibration of the deconvolved difference from normal may be performed and thus produce reported thicknesses with greater accuracy on the edge of the substrate.

Subsequently, a mass may be derived by correlating a set of current responses to a set of thickness measurements, integrating the set of thickness measurements across the surface of the substrate (e.g., creating a mathematical function), and multiplying the result by the density of the conductive layer. For example, a correlated conductive film thickness (cm) may be shown as a function $T(r, \theta)$, where r is a radial position (cm) from a center of a substrate, and $\theta$ is an angle from 0 to $2\pi$. A conductive film mass $CF_{derived}$ may then be derived as follows:

$$CF_{derived} = \rho_{cf} \int_0^{2\pi} \int_0^r T(r, \theta) r dr d\theta \qquad \text{EQUATION 1}$$

where $\rho_{cf}$ is a conductive film density (grams/cm$^3$). In a common independent mass measuring method, a scale is used. Subsequently, for a substrate with a pre-processed mass (e.g., without a substantial presence of the conductive film) in grams of $S_{pre}$, a post-processed mass (e.g., with a substantial presence of the conductive film) in grams of $S_{post}$, the measure mass $CF_{measured}$ may be shown as:

$$CF_{measured} = S_{post} - S_{pre} \qquad \text{EQUATION 2}$$

Thus, the amount of metal penetration (or mass variation) MP in grams may be represented as:

$$MP = CF_{measured} - CF_{derived} \qquad \text{EQUATION 3}$$

In an embodiment, conductive film thickness must be determined with at least two integrals (e.g., two mathematical functions). In general, eddy current to thickness correlation is imprecise close to an edge of a substrate. As previously stated, eddy current measurements generally assume an infinite plane of conductive film. For example, one method of eddy current measurements is to consider an infinite plane of conductive film placed a certain proximity to a set of parallel eddy current sensors. Usually the desired sensor system reported output is the film thickness, where factors such as conductivity, connectivity, grain structure, etc. are assumed to be constant, or alternatively, to have a negligible effect on the raw measured eddy current signal.

However, common methods of eddy current measurement presume the lack of edge effects to create eddy current discontinuities. In practice, this assumption tends only to exists in the center area of the substrate (center zone), since a portion of dies on the substrate surface may be placed near the substrate edge (edge zone) where the eddy current discontinuity may exist.

In a non-obvious way, an eddy current sensor may be positioned off the substrate at a location in which a first alternating electromagnetic field generated by the sensor coil may still interact with the metal film on the edge of the substrate to produce a second alternating electromagnetic field that may subsequently be measured. In general, by isolating the eddy current sensor off the substrate, only the edge portion (edge zone) of the metal film is measured on the substrate, since film present in the center of the substrate (center zone) may have substantially less influence on the second alternating electromagnetic field.

In addition, since the presumed condition of an infinite plane of conductive film is generally not present on the substrate edge, a different set of calibration curves may be needed. In general, depending on the desired zone of interest on the substrate (i.e., center, edge, etc.) the appropriate calibration curve is used.

Subsequently, a set of masses may be derived by correlating at least two sets of current responses (i.e., center zone, edge zone, etc.) to a set of thickness measurements, integrating each set of thickness measurements across the surface of the substrate, and multiplying the result by the density of the conductive layer. For example, in a center zone, a correlated conductive film thickness (cm) may be shown as a function $T_{center}(r_{center}, \theta)$, where $r_{center}$ is a radial distance (cm) from a center of a substrate to the boundary between a center zone and an edge zone, and $\theta$ is an angle from 0 to $2\pi$. A center zone conductive film mass $CF_{center-derived}$ may then be derived as follows:

$$CF_{center-derived} = \rho_{cf} \int_0^{2\pi} \int_0^{r_{center}} T(r, \theta) r dr d\theta \qquad \text{EQUATION 4}$$

where $\rho_{cf}$ is a conductive film density (grams/cm$^3$). Likewise, in an edge zone, a correlated conductive film thickness (cm) may be shown as a function $T'(r, \theta)$, where $r_{edge}$ is a radial distance (cm) between a center zone and edge zone boundary, and a position off the substrate where the eddy current response is substantially zero, and $\theta$ is an angle from 0 to $2\pi$. An edge zone conductive film mass $CF_{edge-derived}$ may then be derived as follows:

$$CF_{edge-derived} = \rho_{cf} \int_0^{2\pi} \int_{r_{center}}^{r_{edge}} T'(r, \theta) r dr d\theta \qquad \text{EQUATION 5}$$

For a substrate with a pre-deposition total mass (e.g., without a substantial presence of the conductive film) in grams of $S_{pre-depo}$, a post-deposition total mass (e.g., with a substantial presence of the conductive film) in grams of $S_{post-depo}$, the measured total mass of the conductive film $CF_{measured}$ may be shown as:

$$CF_{measured} = S_{post-depo} - S_{pre-depo} \qquad \text{EQUATION 6}$$

Thus, the amount of total metal penetration (or mass variation) MP in grams may be represented as:

$$MP \approx CF_{measured} - CF_{center-derived} - CF_{edge-derived} \qquad \text{EQUATION 7}$$

In an embodiment, a localized mean thickness of a conductive film (i.e., Cu, etc.) in an edge zone may be determined. As previously stated, common methods of eddy current measurement presume the lack of edge effects to create eddy current discontinuities. In practice, this assumptions tends only to exist in the center area of the substrate (center zone), since a portion of dies on the substrate surface may be placed near the substrate edge (edge zone) where the eddy current discontinuity may exist.

Assuming that the amount of metal penetration MP (grams), as described above, is relatively small when compared to the overall mass of the conductive film, then $$CF_{edge} \approx CF_{measured} - CF_{center-derived} \quad \text{EQUATION 8}$$

$$t_{mean-edge} \approx CF_{edge}(1/\rho_{cf})(1/SA_{edge-zone}) \quad \text{EQUATION 9}$$

where $SA_{edge-zone}$ is the surface area of the substrate edge zone (cm$^2$), and $\rho_{cf}$ is a conductive film density (grams/cm$^3$).

In general, a substrate by substrate edge correction factor $\beta$ can be generated from combination of EQUATION 8 with EQUATION 5 to maintain the spatial distribution of the conductive layer reported by eddy current measurements, but corrected for mis-calibration of the eddy current sensor:

$$CF_{edge}/C_{edge-derived} = \beta \quad \text{EQUATION 10}$$

giving an mass compensated improved eddy current reported thickness:

$$T_{edge-weight-corrected} = \beta T'(r,\theta) \quad \text{EQUATION 11}$$

In an embodiment, the conductive film thickness may be calibrated based on a derived temperature. In general, a substrate's measured mass is independent of temperature, but usually requires some physical contact, while a substrate's eddy current derived mass generally requires no physical contact, but is dependent on temperature. In addition, eddy current signal variation tends to be primarily proportional to the inverse of conductive film resistivity, which tends to be dependent on temperature. Subsequently the change in resistivity from a reference temperature tends to be proportional to the change in temperature. The proportionality constants and resistivity temperature coefficients are generally known for the materials of interest in substrates. For copper films near room temperature, for example, a lower temperature will generally increase conductivity (e.g., decrease resistivity) which tends to increase the resulting the eddy current response, and hence the derived conducting film thickness. While a higher temperature will generally correlated to a smaller thickness.

Generally, since contacting the substrate with a temperature probe (i.e., thermal couple, resistance temperature detector, etc.) may also increase the amount of processing time for each substrate, and hence reduce overall throughput, other temperature measuring techniques are desired. It may also be undesirable to touch the surface of the substrate. Other optical means of determining temperature depend on the emissivity of the films which are notoriously difficult to control either due to surface preparation or simply different substrates have different films. In a non-obvious way, the difference between the conductive film derived mass and the conductive film measured mass may be used to offset the eddy current measurement in order to more accurately derive a conductive film thickness or a conductive film derived mass.

For example during calibration of the eddy current sensors, a reference substrate may be measured for a temperature, the mass of conductive film (as shown in EQUATION 6), and a set of eddy current responses at a corresponding set of particular thickness positions on the substrate. As previously stated, since conductive film resistivity (which tends to be dependent on temperature) is inversely related to eddy current signal variation, any substantive changes in eddy current responses for the same substrate at an unknown temperature, may be caused a change in the substrate temperature. Subsequently, the ratio of the reference sample measurements can be used as a factor to correct the eddy current measurement of other similarly configured substrates. The mass measurements provide a means to confirm or set error limits on the similarity of the unknown substrate being measured compared to the substrate calibration set.

In an embodiment, the penetration of a conductive film into substrate pores, or the subsequent creation of voids in the substrate, may be detected by comparing the independently measured mass of a conductive film to a correlated mass of the eddy current response to the conductive film. In an embodiment, the substrate comprises a substantially porous low k material. Since small amounts of isolated conductive material may not generate a measurable eddy current response or at least a significantly reduced signal as expected from the measured mass, any conductive material that may have penetrated into the dielectric pores (and may have also subsequently created voids in the conductive film) would appear in the physically measured mass number, but not in the correlated mass number. That is, given the pre and post-mass difference in the substrate, and pre and post eddy current signal responses on a substrate undergoing deposition or metal removal, voids may be detected in the patterned material or penetration of metal into dielectric pores.

In an embodiment, conductive film overburden (e.g., excessive conductive film thickness) may be determined. For example, in general, a greater continuous mass of conductive film, such as with connected overburden, creates a larger eddy current response, than that for disconnected masses, such as for a conductive film in a via or trench. Measuring the mass of the substrate both before and after a film removal by any means (CMP, electro polish, electrochemical mechanical polishing, etch, etc.) it may shown the mass of material removed to form the vias and trenches may be determined. By subtracting this mass from the conductive film derived mass, the conductive film overburden may be calculated, which may in turn be used to calculate an average overburden thickness or as a fault detection method.

Assuming that the amount of metal penetration MP (grams), as described above, is relatively small when compared to the overall mass of the conductive film, then for a post-etch substrate mass of $S_{post-etch}$ (g), a pre-etch substrate mass of $S_{pre-etch}$ (g), the mass difference of material ($VT_{measured}$) removed is:

$$VT_{measured} = S_{pre-etch} - S_{post-etch} \quad \text{EQUATION 12}$$

If $\rho_{cf}$ is a conductive film density (grams/cm$^3$), $CF_{pre-center-derive}$ is a pre-etch center zone conductive film derived mass as shown in EQUATION 4, and $CF_{pre-edge-derive}$ is a pre-etch edge zone conductive film derived mass as shown in EQUATION 5, then the mass of conductive film overburden $CFO_{derived}$ is:

$$CFO_{pre-derived} \approx CF_{pre-enter-derived} + CF_{pre-edge-derived} \quad \text{EQUATION 13}$$

Similarly the post etch substrate conductive film mass can be calculated based on post-etch measurements to calculate $CFO_{post-derived}$. These two eddy current derived masses may be used to find the derivied mass difference of material ($VT_{derived}$) removed as:

$$VT_{derived} = CFO_{pre-derived} - CF_{post-derived} \quad \text{EQUATION 14}$$

Since the eddy current signal is predominantly sensitive to the connected overburden film, $VT_{derived}$ will tend to approach the mass of the total overburden as the film removal process is completed, but will not change after all the overburden is removed. For many substrate processes, such as damascene interconnect process flows, it is desirable for conductive film in the vias and/or trenches to remain, although some amount of over-processing time is often required to reduce shorting from remaining overburden.

The difference between the mass measured and the eddy current derived masses provides a measure of the amount of overburden likely on the substrate or can be used as a SPC (statistical process control) or fault detection metric for processing. $VT_{derived}-VT_{measured}$ should be about zero for processing that stops with overburden remaining since both measurements have nearly constant sensitivity to overburden. If $VT_{derived}-VT_{measured}$ is less than zero, then more conductive film mass was removed than just the overburden. An average conductive film loss in the trenches may be determined assuming only conductive film was lost. (Additional modifications taking into account loss of the much lighter dielectric film between the trenches can be simply accommodated).

Average thickness of conductive film loss in the trenches, sometimes called dishing or total Cu loss, $t'_{derived}$ may then be derived as $$t_{derived}' \approx (VT_{measured} - VT_{derived})(1/\rho_{cf})(1/OA) \qquad \text{EQUATION 15}$$

where OA is the surface area of the substrate (cm$^2$) open to the conductive film (traditionally called the open area), and $\rho_{cf}$ is a conductive film density (grams/cm$^3$).

If $VT_{derived}-VT_{measured}$ is greater than zero, then the eddy current signal may be more detectable, subsequently flagging issues such as significant film resistivity deviations, remaining overburden, or significant shorting between damaged lines. Note that although pre-deposition, post-deposition, pre-etch and post-etch masses may be used to derive estimates of conductive film addition and removal, the combination with eddy current data allows discrimination based on either spatial information of the film thickness and/or discrimination between overburden film and film in less electrically connected configurations on a macro or microscopic scale.

In an embodiment, a trench/via barrier thickness may be determined. In general, barrier material (e.g., TiN, TaN, etc.) is substantially less conductive than conductive film (e.g., Cu, etc.). By measuring the mass of the substrate both before and after the combined barrier and conductive film deposition, the combined mass of the barrier and conductive film deposition may be determined. However, an eddy current measurement of this combined mass would predominantly only measure the conductive film, and not the barrier material. Subtracting the derived conductive film mass from the combined measured barrier and conductive film deposition would yield a derived mass of only the barrier. By dividing the barrier derived mass by the barrier density, a barrier area may be determined. Subsequently, dividing this barrier area by the via and trench aggregate opening area yields an average via and trench barrier thickness.

Assuming that the amount of metal penetration MP (grams), as described above, is relatively small when compared to the overall mass of the conductive film, then for a post-etch substrate mass of $S_{post-deposition}$ (g), a pre-etch substrate mass of $S_{pre-deposition}$ (g), the combined mass of via and trench material and conductive film $CFB_{measured}$ added is:

$$CFB_{measured} = S_{post-depo} - S_{pre-depo} \qquad \text{EQUATION 16}$$

If $CF_{center-derive}$ is a center zone conductive film derived mass as shown in EQUATION 4, and $CF_{edge-derive}$ is a edge zone conductive film derived mass as shown in EQUATION 5, then the derived mass of barrier material $B_{derived}$ is:

$$B_{derived} \approx CFB_{measured} - (CF_{center-derived} + CF_{edge-derived}) \qquad \text{EQUATION 17}$$

If BA is the aggregate area of via and trench opening surfaces (cm$^2$), and $\rho_b$ is a barrier material density (grams/cm$^3$), then average barrier thickness $t''_{derived}$ may then be derived as:

$$t_{derived}'' \approx B_{derived}(1/\rho_b)(1/BA) \qquad \text{EQUATION 18}$$

In an embodiment, center of mass and moments of inertia about center of mass (inertia ellipsoid) can be calculated and the compared to calculated values from eddy current spatial data to produce sensitive global uniformity metrics. These metrics may be derived independently or used in tandem to jointly calibrate a mass and eddy current metrology system. For example, assuming a substrate of radius R with some measured value val(x,y) such as eddy current signal as a function of position on the substrate. By considering the value as a mass density one may calculate a number of metrics that characterize the spatial distribution of the value across the substrate. In this particular case, the eddy current and known mass density of the film can actually generate a true measure of mass density across the substrate. Pre and post measurements or appropriate solid uniform disk approximations can be used to include or exclude the effects of the substrate mass as appropriate.

Mass, as shown in EQUATION 1, may be expressed in slightly more general form:

$$\text{Mass} := \int_0^{2\pi} \int_0^1 \text{val}(r \cdot \cos(\theta), r \cdot \sin(\theta)) \cdot r \, dr \, d\theta \qquad \text{EQUATION 19}$$

Additional metrics can be derived using analogy with mechanical concepts of moment of inertia. The analogy with classical mechanics is useful because many properties of the integrals have been proven already and mechanical analogies are easier to interpret physically when trying to solve problems flagged by such metrics.

In general, moments of inertia are calculated by performing integrals over the substrate area of the value used as the mass density surrogate times the perpendicular distance of the integrated element from the axis in question. Higher order moments can be calculated by raising the perpendicular distance to powers greater than one. For example, an example of a metric derived a mass density Uval(x,y) based on the moment of inertial about the x-axis can be calculated by:

$$UXcm := \frac{\int_0^{2\pi} \int_0^1 U\text{val}(r \cdot \cos(\theta), r \cdot \sin(\theta)) \cdot r \cdot \cos(\theta) \cdot r \, dr \, d\theta}{UMass} \qquad \text{EQUATION 20}$$

where the distance to the x-axis which may be x which is r cos (theta) in polar coordinates.

It may be found to be beneficial to measure the substrate by supporting the substrate in more than one location (e.g., a triangle of points at the edge of the substrate). The measured mass carried by each support is determined by well known static mechanics equations involving integrals of the mass density across the substrate. Hence the measured mass is the solution of the integral, but the eddy current provides the spatial information. By themselves, a small number of mass measurements will only provide crude estimates of various spatial film deposition thicknesses despite the great accuracy available for the individual measurements. Combined with the eddy current spatial information and the static mechanics integrals, the simpler and maybe faster or cheaper mass based measurements may be calibrated to correspond to known spatial faults in typical plating or CMP (chemical mechanical polishing) systems.

Figure 4:
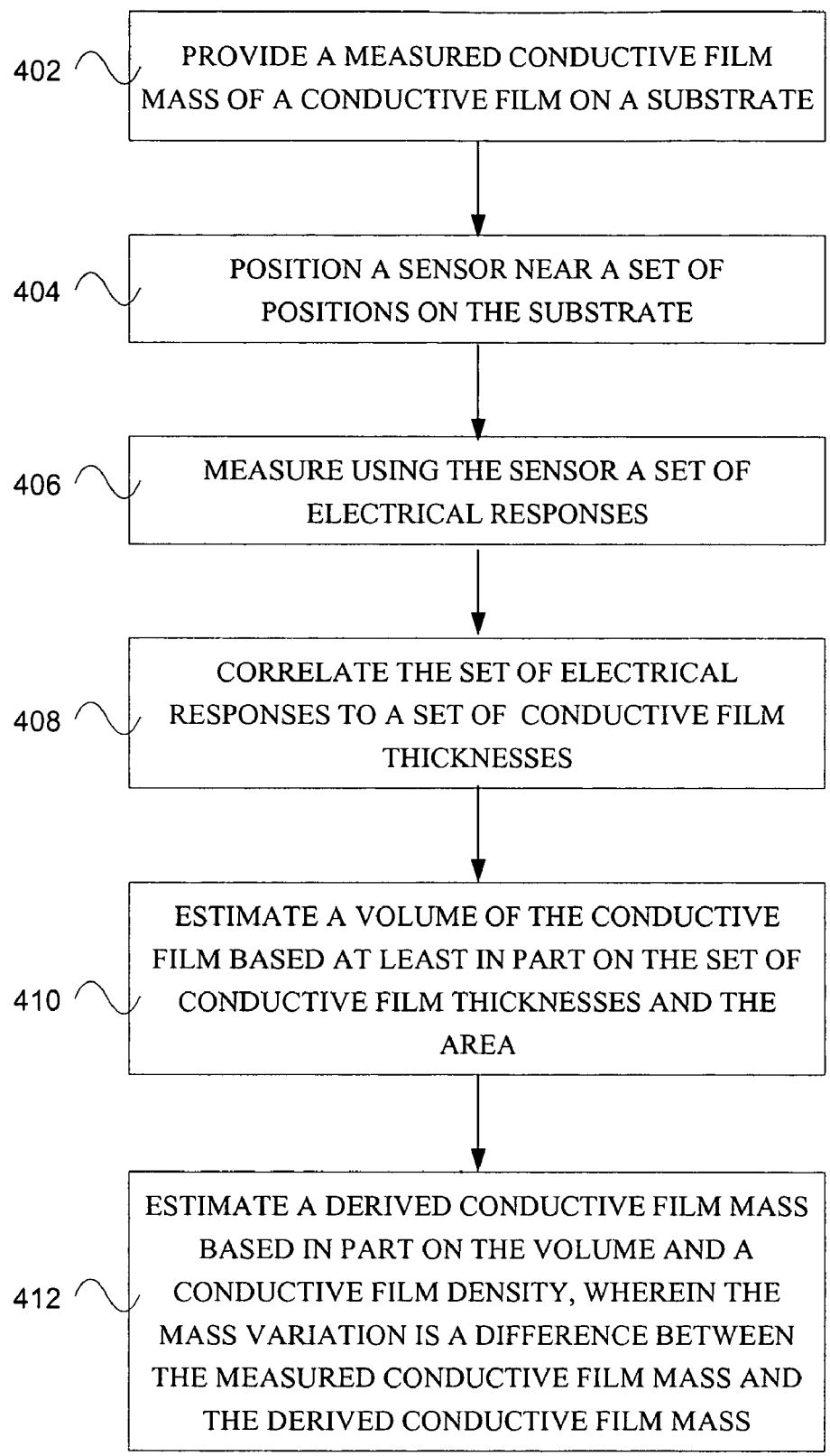
FIG. 4 illustrates a simplified set of steps for determining a mass variation of a conductive film on a substrate with an area, an edge zone, and a center zone.

Referring now to FIG. 4, a simplified set of steps for determining a mass variation of a conductive film on a substrate with an area, an edge zone, and a center zone is shown, according to one embodiment of the invention. Initially, at step 402, a measured conductive film mass of a conductive film on a substrate is provided. A sensor is then positioned near a set of positions on the substrate, at step 404. Next, a set of electrical responses is measured using the sensor, at step 406. The set of electrical responses is then correlated to a set of conductive film thicknesses, at step 408. Next, a volume of the conductive film is estimated based at least in part on the set of conductive film thicknesses and the area, at step 410. Finally, a derived conductive film mass is estimated based in part on the volume and a conductive film density, wherein the mass variation is a difference between the measured conductive film mass and the derived conductive film mass, at step 412.

While this invention has been described in terms of several preferred embodiments, there are alterations, permutations, and equivalents which fall within the scope of this invention. It should also be noted that there are many alternative ways of implementing the methods of the present invention.

Advantages of the invention include methods and apparatus for measuring morphology of a conductive film on a substrate. Additional advantages include the use of simple inexpensive eddy current sensors, the reduction of required measurements to accurately measure film thickness.

Having disclosed exemplary embodiments and the best mode, modifications and variations may be made to the disclosed embodiments while remaining within the subject and spirit of the invention as defined by the following claims.

What is claimed is:

1. A method of determining a mass variation of a conductive film on a substrate with an area, an edge zone, and a center zone, comprising:
    providing a measured conductive film mass of a conductive film on a substrate;
    positioning a sensor near a set of positions on said substrate;
    measuring using said sensor a set of electrical responses;
    correlating said set of electrical responses to a set of conductive film thicknesses;
    estimating a volume of said conductive film based at least in part on said set of conductive film thicknesses and said area;
    estimating a derived conductive film mass based in part on said volume and a conductive film density, wherein said mass variation is a difference between said measured conductive film mass and said derived conductive film mass.

2. The method of claim 1, wherein said step of estimating a volume includes creating a mathematical function of said set of conductive film thicknesses as a function of a radius and an angle.

3. The method of claim 1, wherein said step of estimating a volume includes creating a center zone mathematical function of said set of conductive film thicknesses as a first function of a first radius and a first angle, and an edge zone mathematical function of said set of conductive film thicknesses as a second function of a second radius and a second angle.

4. The method of claim 1, wherein said measuring a set of electrical responses includes one of measuring voltages and measuring current.

5. The method of claim 1, wherein said step of correlating said set of electrical responses includes providing a set of thickness correlation curves at a set of sensor position radii from a center of the substrate to a position where a sensitivity of said sensor to said edge zone is greater than zero.

6. The method of claim 5, wherein each of said set of thickness correlation curves is created with a mathematical optimization function.

7. The method of claim 1, wherein said mass variation is caused by a set of deviations in said conductive film properties.

8. The method of claim 7, wherein said set of deviations in said conductive film properties includes one of a set of different grain sizes after annealing, a different additive, a set of concentrations in a plater, a set of changes in a plating recipe, a rough substrate surface, a set of substrate voids, and an overburden.

9. The method of claim 8, wherein said set of deviations is used to measure a penetrated mass of said conductive film into a dielectric material.

10. The method of claim 9, wherein said dielectric material is a substantially porous low k material.

11. The method of claim 8, wherein said set of deviations is used to measure an overburden mass of said overburden.

12. The method of claim 8, wherein said set of deviations is used in a statistical process control of a plating process.

13. The method of claim 1, wherein said set of electrical responses is calibrated based on temperature.

14. The method of claim 13, wherein said temperature is used to compensate for a set of temperature variations during said step of measuring using a said sensor.

15. The method of claim 1, wherein said step of estimating a volume of said conductive film includes calibrating said thickness based at least in part on a ratio of a substrate center zone mass and a substrate edge zone mass.

16. The method of claim 15, wherein said mass variation is used to improve a precision of a set of edge zone conductive film thicknesses.

17. The method of claim 1, wherein said mass variation is used to provide in a process that includes a temperature compensation, one of a validation, a statistical process control, and a self-consistency.

18. A method of determining a mass variation of a conductive film on a substrate with an area and a measured conductive film mass, comprising:
    measuring a set of electrical responses to said conductive film;
    correlating said set of electrical responses to a set of conductive film thicknesses;
    estimating a volume of said conductive film based at least in part on said set of conductive film thicknesses and said area;
    estimating a derived conductive film mass based in part on said volume and a conductive film density, wherein said mass variation is a difference between said measured conductive film mass and said derived conductive film mass.

19. An apparatus for determining a mass variation of a conductive film on a substrate with an area and a measured conductive film mass, comprising:
    means for measuring a set of electrical responses of said conductive film;
    means for correlating said set of electrical responses to a set of conductive film thicknesses;
    means for estimating a volume of said conductive film based at least in part on said set of conductive film thicknesses and said area;

means for estimating a derived conductive film mass based in part on said volume and a conductive film density, wherein said mass variation is a difference between said measured conductive film mass and said derived conductive film mass.

20. The apparatus of claim 19, wherein said means for estimating a volume includes a means for creating a mathematical function of said set of conductive film thicknesses as a function of a radius and an angle.

21. The apparatus of claim 20, wherein said set of electrical responses includes one of a set of voltages and a set of currents.

22. The apparatus of claim 21, wherein said means for correlating said set of electrical responses includes a means of providing a set of thickness correlation curves at a set of sensor position radii from a center of the substrate to a position where a sensitivity of said sensor to said edge zone is greater than zero.

23. The apparatus of claim 22, wherein each of said set of thickness correlation curves is created with a mathematical optimization function.

24. The apparatus of claim 23, wherein said set of electrical responses is calibrated based on a temperature.

25. The apparatus of claim 24, wherein said means for estimating a derived conductive film mass includes a means for calibrating said thickness based at least in part on a ratio of a substrate center zone mass and a substrate edge zone mass.

* * * * *